(12) United States Patent
Xu et al.

(10) Patent No.: US 11,344,851 B2
(45) Date of Patent: *May 31, 2022

(54) BIOLOGICAL FLUID SEPARATION DEVICE

(71) Applicant: BECTON DICKINSON AND COMPANY, Franklin Lakes, NJ (US)

(72) Inventors: Qihua Xu, Cary, NC (US); Kristin Weidemaier, Raleigh, NC (US); Christopher Basciano, Apex, NC (US); Sivaramakrishnan Balasubramanian, Morrisville, NC (US); Patrick Downie, Apex, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/658,350

(22) Filed: Oct. 21, 2019

(65) Prior Publication Data

US 2020/0047134 A1 Feb. 13, 2020

Related U.S. Application Data

(63) Continuation of application No. 15/447,859, filed on Mar. 2, 2017, now Pat. No. 10,493,409.

(Continued)

(51) Int. Cl.
*B01D 63/08* (2006.01)
*G01N 33/49* (2006.01)
(Continued)

(52) U.S. Cl.
CPC .............. *B01D 71/50* (2013.01); *B01D 63/02* (2013.01); *B01D 63/08* (2013.01); *G01N 33/491* (2013.01);
(Continued)

(58) Field of Classification Search
CPC .... B01D 63/08; B01D 63/087; B01D 63/088; B01D 63/085; B01D 69/06; B01D 71/50;
(Continued)

(56) References Cited

U.S. PATENT DOCUMENTS

| 4,066,554 A | 1/1978 | Guyer |
| 4,212,742 A | 7/1980 | Solomon et al. |

(Continued)

FOREIGN PATENT DOCUMENTS

| CN | 104107561 A | 10/2014 |
| EP | 0403031 A2 | 12/1990 |

(Continued)

OTHER PUBLICATIONS

Office Action received in corresponding EP Appl. No. 16731437.6 dated Jan. 15, 2020 (5 pages).

(Continued)

*Primary Examiner* — Pranav N Patel
(74) *Attorney, Agent, or Firm* — Botos Churchill IP Law LLP

(57) ABSTRACT

A biological fluid separation device adapted to receive a biological fluid sample having a first portion and a second portion is disclosed. The device includes a housing having a first chamber having a first chamber inlet for receiving the biological fluid sample therein and a first chamber outlet. The housing has a second chamber having a second chamber inlet and a second chamber outlet, and a separation member separating at least a portion of the first chamber outlet and the second chamber. The separation member is adapted to restrain the first portion of the biological fluid sample within the first chamber and to allow at least a portion of the second portion of the biological fluid sample to pass into the second chamber. An actuator, such as a vacuum source, draws the (Continued)

biological fluid sample into the first chamber and the second portion into the second chamber.

11 Claims, 10 Drawing Sheets

Related U.S. Application Data

(60) Provisional application No. 62/302,296, filed on Mar. 2, 2016.

(51) Int. Cl.
| | | |
|---|---|---|
| *B01D 71/50* | (2006.01) | |
| *B01D 63/02* | (2006.01) | |
| *A61M 1/16* | (2006.01) | |
| *A61M 1/34* | (2006.01) | |
| *B01D 29/00* | (2006.01) | |
| *B01D 69/06* | (2006.01) | |

(52) U.S. Cl.
CPC .............. *A61M 1/16* (2013.01); *A61M 1/34* (2013.01); *A61M 2205/3331* (2013.01); *B01D 29/0004* (2013.01); *B01D 69/06* (2013.01)

(58) Field of Classification Search
CPC .......... B01D 2313/086; B01D 29/0004; B01D 29/0095; B01D 29/01; B01D 29/05; A61M 1/16; A61M 1/1631; A61M 1/34; A61M 2205/3331; A61M 2205/3334; A61M 2205/3355; A61M 2202/0413; A61M 2202/0415; G01N 33/491
IPC ................ B01D 63/08,63/087, 63/088, 63/085, 69/06, 71/50, 2313/086, 29/004, 29/0095, 29/01, 29/05; A61M 1/16, 1/1631, 1/34, 2205/3331, 2205/3334, 2205/3355, 2202/0413, 2202/0415; G01N 33/491
See application file for complete search history.

(56) References Cited

U.S. PATENT DOCUMENTS

| | | | |
|---|---|---|---|
| 4,343,705 A | 8/1982 | Legg | |
| 4,740,313 A | 4/1988 | Schoendorfer et al. | |
| 4,769,150 A | 9/1988 | Ramstack | |
| 4,871,462 A | 10/1989 | Fischel et al. | |
| 4,980,297 A | 12/1990 | Haynes et al. | |
| 5,034,135 A | 7/1991 | Fischel | |
| 5,100,376 A | 3/1992 | Blake | |
| 5,922,210 A | 7/1999 | Brody | |
| 6,010,627 A | 1/2000 | Hood | |
| 6,153,104 A | 11/2000 | Robertson | |
| 8,889,071 B2 | 11/2014 | Aota et al. | |
| 2004/0251214 A1 | 12/2004 | Adams | |
| 2005/0261642 A1 | 11/2005 | Weston | |
| 2007/0151924 A1 | 7/2007 | Mir et al. | |
| 2008/0272283 A1 | 11/2008 | Feldsine et al. | |
| 2010/0285573 A1 | 11/2010 | Leck | |
| 2011/0058983 A1* | 3/2011 | Gadrat ...................... A61P 7/00 422/44 |
| 2011/0155667 A1 | 6/2011 | Charest | |
| 2012/0291867 A1 | 11/2012 | Gassman | |
| 2013/0015119 A1 | 1/2013 | Pugh et al. | |
| 2013/0334139 A1 | 12/2013 | Blickhan | |
| 2014/0042094 A1 | 2/2014 | Montagu | |
| 2014/0217027 A1 | 8/2014 | Meyer | |
| 2014/0305196 A1 | 10/2014 | Ellis et al. | |
| 2014/0305197 A1 | 10/2014 | Fletcher et al. | |
| 2014/0308167 A1 | 10/2014 | Fletcher et al. | |
| 2014/0309556 A1 | 10/2014 | Fletcher et al. | |
| 2015/0060363 A1 | 3/2015 | Kusters et al. | |
| 2015/0152467 A1 | 6/2015 | Ingber et al. | |
| 2016/0074569 A1 | 3/2016 | Schuetz | |

FOREIGN PATENT DOCUMENTS

| | | |
|---|---|---|
| EP | 0464707 A2 | 1/1992 |
| EP | 2516320 A1 | 10/2012 |
| EP | 2524708 A3 | 10/2013 |
| EP | 2842619 A1 | 3/2015 |
| JP | 57104862 | 6/1982 |
| JP | 61172060 S | 8/1986 |
| JP | S63224703 A | 9/1988 |
| JP | HEI03247345 | 11/1991 |
| JP | H0910299 A | 1/1997 |
| JP | 2010237050 A | 10/2003 |
| JP | 2004503745 A | 2/2004 |
| JP | 2005529746 A | 10/2005 |
| KR | 20020061895 A | 7/2002 |
| WO | 19910001796 A1 | 2/1991 |
| WO | 9614578 A1 | 5/1996 |
| WO | 9624425 A1 | 8/1996 |
| WO | 20000050157 A1 | 8/2000 |
| WO | 0112325 A1 | 2/2001 |
| WO | 2011066498 A2 | 6/2011 |
| WO | 2012125460 A1 | 9/2012 |
| WO | 2014023765 A2 | 2/2014 |
| WO | 2014095058 A1 | 6/2014 |
| WO | 20150014934 A1 | 2/2015 |
| WO | 2016200806 A1 | 12/2016 |

OTHER PUBLICATIONS

Office Action received in corresponding CN Appl. No. 2017800227248 dated Jul. 3, 2020 (11 pages).

Wang Z F et al: "Seamless joining of porous membrane with thermoplastic microfluidic devices", Microelectronic Engineering, vol. 110, XP028673721, ISSN: 0167-9317, DOI: 10.1016/J.MEE. 2013.02.074, pp. 386-391.

Chinese Office Action received in 201780048849.8 dated Nov. 21, 2019, pp. 15.

International Search Report and Written Opinion for Application No. PCT/US2017/036747 dated Nov. 21, 2017.

ISR and Written Opinion for Application No. PCT/US2016/036209 dated Aug. 25, 2016.

Jaffrin My: Innovative Processes for Membrane Plasma Separation 11, Journal of Membrane Science, Elsevier BV, NL, vol. 44, No. 1, Jun. 1, 1989 (Jun. 1, 1989), pp. 115-129, XP000068839, ISSN: 0376-7388, DOI: 10.1016/S0376-7388(00)82344-3, pp. 123-124.

Japanese Official Notice of Rejection issued in corresponding JP application No. 2017-563527 dated Oct. 23, 2018.

Japanese Office Action issued in corresponding JP application No. 2017-564128 dated Nov. 13, 2018, pp. 5.

Japanese Notice of Refusal issued in corresponding Japanese Patent Application No. 2018-545826 dated Feb. 2, 2021.

First Examination Report issued in corresponding Indian Patent Application No. 201817047315, dated May 31, 2021, 55 pp.

Notice of Rejection issued in Japanese Application No. 2020-000574 dated Mar. 2, 2021.

Office Action issued in corresponding Japanese Patent Application No. 2018-564216 dated Jun. 3, 2021, 8 pp.

Office Action issued in corresponding EP Patent Application No. 17713096.0 dated Feb. 1, 2022, 8 pp.

Office Action issued in corresponding Japanese Patent Application No. 2018-564216 dated Dec. 14, 2021, 6 pp.

Office Action issued in corresponding European Patent Application No. 1773181.1 dated Apr. 4, 2022, (7 pages).

* cited by examiner

| DEVICE # | INPUT VOL. mL | OUPUT VOL. μL | PLASMA PIC | HEMOGLOBIN mg/dL |
|---|---|---|---|---|
| 1 | 2.6 | 477.8 | | |
| 2 | 2.2 | 331.2 | | 12.9 |
| 3 | 2.8 | 376.2 | | |
| 4 | 3 | 435.7 | | |
| 5 | 3 | 331.9 | | 8.4 |
| 6 | 3 | 416.1 | | |
| 7 | 3 | 482.6 | | |
| 8 | 3 | 335.1 | | 12.6 |
| 9 | 3 | 475.3 | | |
| CONTROL | - | - | | 3.8 |

FIG. 5

| | INPUT WHOLE BLOOD | PLASMA CONTRL | PLASMA SAMPLE 1 | PLASMA SAMPLE 2 | PLASMA SAMPLE 3 |
|---|---|---|---|---|---|
| WBC, x10$^3$/μL | 4.5 | 0.1 | 0.1 | 0.1 | 0.1 |
| RBC, x10$^3$/μL | 5.36 | 0.00 | 0.00 | 0.00 | 0.00 |
| PLT, x10$^3$/μL | 131 | 0 | 0 | 0 | 0 |
| HCT, % | 46 | 0.0 | 0.0 | 0.0 | 0.0 |

FIG. 6

| DEVICE # | INPUT VOL. mL | OUPUT VOL. μL |
|---|---|---|
| 1 | 2.8 | 208.7 |
| 2 | 2.7 | 233.9 |
| 4 | 3 | 248.5 |
| 5 | 3 | 256.3 |
| 6 | 3 | 261.2 |
| 7 | 3 | 235.9 |
| 8 | 3 | 268.9 |

BIOLOGICAL FLUID SEPARATION DEVICE

CROSS-REFERENCE TO RELATED APPLICATION

This application is a continuation of U.S. application Ser. No. 15/447,859, filed on Mar. 2, 2017, which claims priority to U.S. Provisional Application Ser. No. 62/302,296, entitled "Biological Fluid Separation Device", and filed Mar. 2, 2016, the entire disclosures of which are hereby incorporated by reference.

BACKGROUND OF THE INVENTION

1. Field of the Disclosure

The present disclosure relates generally to devices adapted for use with biological fluids. More particularly, the present disclosure relates to devices adapted for separating components of biological fluids.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Blood samples contain a whole blood portion and a plasma portion. Plasma separation from whole blood has been traditionally achieved by centrifugation which typically takes 15 to 20 minutes and involves heavy labor or complex work flow. Recently there are other technologies that have been used or tried to separate plasma such as sedimentation, fibrous or non-fibrous membrane filtration, lateral flow separation, microfluidics cross flow filtration, and other microfluidics hydrodynamic separation techniques. However, many of those technologies have various challenges arranging from poor plasma purity, analyte bias or requiring specific coating to prevent analyte bias, high hemolysis, requiring dilution, long separation time, and/or difficulty in recovering the plasma. For example, most membrane based separation technologies suffer from an analyte bias problem, and often require specific coating treatments for the target analytes.

SUMMARY OF THE INVENTION

The present disclosure provides a biological fluid separation device, such as a blood separation device, and a separation process that allows high quality plasma to be generated in less than 1 minute. The blood separation device allows a single pressure source such as a vacuum source, for example a vacutainer tube, to power the plasma separation process. The device design is simple, low cost, and disposable. The plasma separation process is fast, easy to operate, and produces high quality plasma samples from whole blood. It is scalable from sample size of micron liters to milliliters. The separation process does not require any hardware or electric power. It is operated by pressures which can be generated by using a syringe draw and/or a vacutainer tube. The quality of the separated plasma is comparable to that of tube plasma generated by centrifugation and suitable for various diagnostic needs.

In accordance with an embodiment of the present invention, a biological fluid separation device is adapted to receive a biological fluid sample having a first portion and a second portion. The biological fluid separation device includes a housing having a first chamber having a first chamber inlet for receiving the biological fluid therein and a first chamber outlet. The housing includes a second chamber having a second chamber inlet and a second chamber outlet, and a separation member separating at least a portion of the first chamber outlet and the second chamber. The separation member is adapted to restrain the first portion of the biological fluid sample within the first chamber and to allow at least a portion of the second portion of the biological fluid portion to pass into the second chamber. The biological fluid separation device also includes an actuator in communication with a portion of the housing, such that actuation of the actuator draws the biological fluid sample into the first chamber.

In certain configurations, the biological fluid is whole blood, the first portion is a red blood cell portion, and the second portion is a plasma portion. During use, actuation of the actuator draws the second portion of the biological fluid through the separation member. The actuator may be a vacuum source, such as a single vacuum source. The vacuum source may be an evacuated tube.

In certain configurations, the second chamber is a plasma collection container. In other configurations, a plasma collection container is provided in communication with the second chamber. The actuator may be a single actuator which imparts a pressure to a portion of the first chamber to draw the biological fluid into the first chamber, and imparts a pressure to a portion of the second chamber to draw a portion of the second portion of the biological fluid into the second chamber.

The separation member may be a track-etched membrane, such as a polycarbonate track-etched membrane. The biological fluid separation device may also include a vent in communication with a portion of the second chamber. The vent may be transitionable between a closed position in which the vent seals the second chamber, and an open position in which the second chamber is vented to atmosphere. The vent may be provided in the closed position during separation of the second portion of the biological fluid sample from the first portion of the biological fluid sample, and in the open position during removal of the second portion of the biological fluid sample from the second chamber.

In accordance with another embodiment of the present invention, a biological fluid separation device is adapted to receive a biological fluid sample having a first portion and a second portion. The biological fluid separation device includes a housing having a first chamber having a first chamber inlet for receiving the biological fluid therein and a first chamber outlet. The housing also includes a second chamber having a second chamber inlet and a second chamber outlet, and a separation member separating at least a portion of the first chamber outlet and the second chamber. The separation member is adapted to restrain the first portion of the biological fluid sample within the first chamber and to allow at least a portion of the second portion of the biological fluid portion to pass into the second chamber. The biological fluid separation device also includes an actuator, a first line in communication with the actuator and the first chamber, and a second line in communication with the actuator and the second chamber. Actuation of the actuator draws the biological sample into the first chamber via the first line, and draws the second portion of the biological sample into the second chamber via the second line.

A single actuator may provide a first pressure to a portion of the first chamber via the first line and a second pressure to a portion of the second chamber via the second line. In certain configurations, the biological fluid is whole blood, the first portion is a red blood cell portion, and the second portion is a plasma portion. The actuator may be a vacuum source, such as a single vacuum source. The vacuum source may be an evacuated tube.

In certain configurations, the second chamber is a plasma collection container. In other configurations, the biological fluid separation device includes a plasma collection container in communication with the second chamber. The separation member may be a track-etched membrane, such as a polycarbonate track-etched membrane.

In certain configurations, the biological fluid separation device also includes a vent in communication with a portion of the second chamber. The vent is transitionable between a closed position in which the vent seals the second chamber, and an open position in which the second chamber is vented to atmosphere. The vent may be provided in the closed position during separation of the second portion of the biological fluid sample from the first portion of the biological fluid sample, and in the open position during removal of the second portion of the biological fluid sample from the second chamber. A porous material may also be disposed within at least a portion of the second line.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a table listing the input blood volume and output plasma volume of performance testing of the device of FIG. 1 in accordance with an embodiment of the present invention.

FIG. 6 is a table listing the input blood volume and quality of the plasma sample void of first component portions achieved through performance testing of the device of FIG. 1 in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
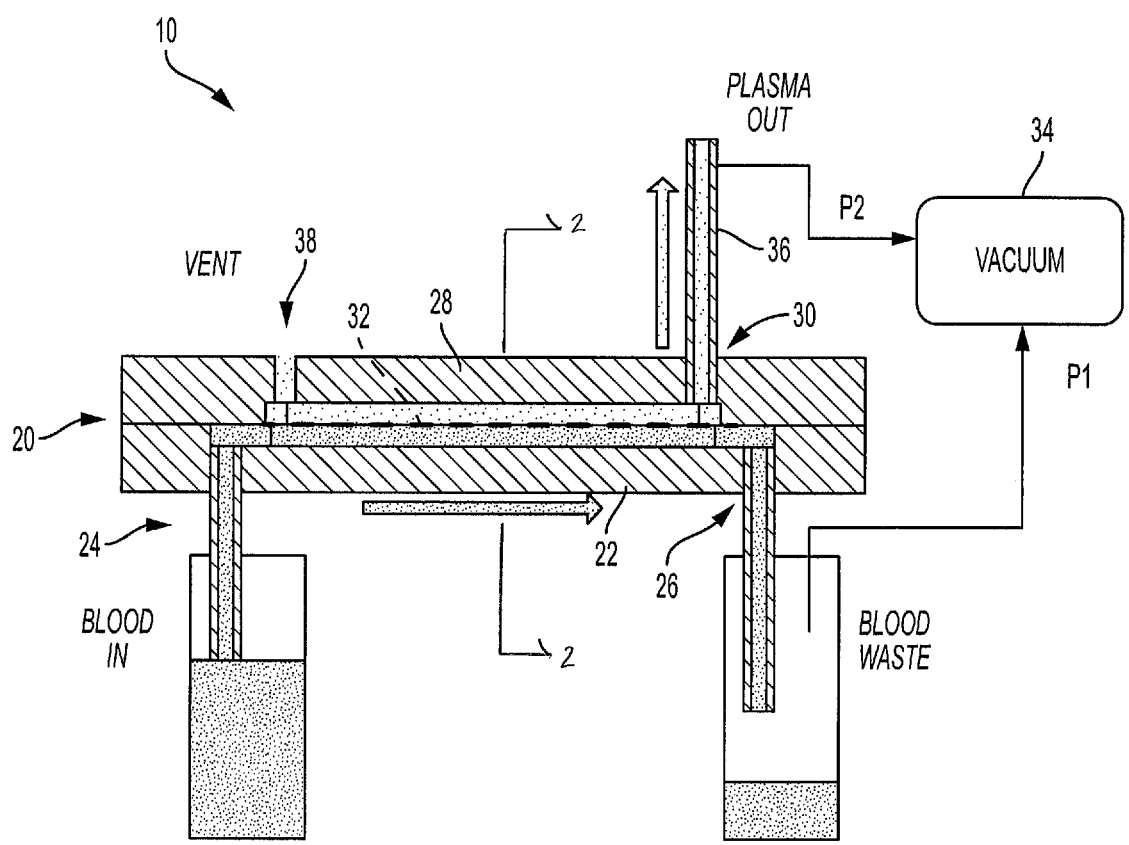
FIG. 1 is a schematic cross-sectional representation of a biological fluid separation device, such as a blood separation device, in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
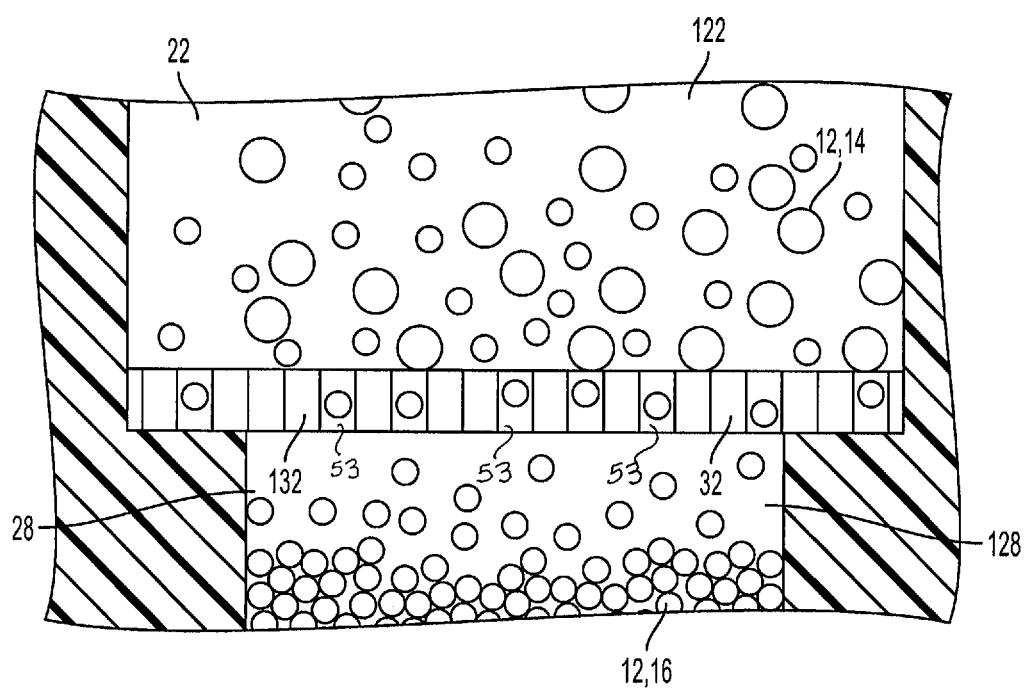
FIG. 2 is a partial cross-sectional view of the separation member of the blood separation device of FIG. 1 taken along line 2-2 in accordance with embodiments of the present invention, with the separation member separating a plasma portion of a blood sample from a whole blood portion of the blood sample.

FIG. 1 illustrates an exemplary embodiment of a biological fluid separation device, such as a blood separation device of the present disclosure. Referring to FIGS. 1 and 2, a blood separation device 10 of the present disclosure is adapted to receive a blood sample 12 having a red blood cell portion 14 and a plasma portion 16. The present disclosure provides a blood separation device and a separation process that allows high quality plasma to be generated in less than 1 minute and a blood separation device that allows a single pressure source such as a vacuum source or a vacutainer tube to power the whole plasma separation process. The device design is simple, low cost, and disposable. The plasma separation process is fast, easy to operate, and produces high quality plasma samples from whole blood. It is scalable from sample size of micron liters to milliliters. The separation process does not require any hardware or electric power. It is operated by pressures which can be generated by using a syringe draw and/or a vacutainer tube. The quality of the separated plasma is comparable to that of tube plasma generated by centrifugation and suitable for various diagnostic needs. After collection of a blood sample, the blood separation device isolates the plasma portion of the blood sample, as will be described herein, and may allow for transfer of the plasma portion of the blood sample to a point-of-care testing device.

Referring to FIGS. 1 and 2, a blood separation device 10 generally includes a housing 20, a first chamber or blood chamber 22, a first chamber inlet 24, a first chamber outlet 26, a second chamber or plasma chamber 28, a second chamber outlet 30, a separation member or membrane 32, an actuator 34, a plasma collection container 36, and a vent 38.

In one embodiment, the housing 20 defines a first chamber 22 and a second chamber 28. The first chamber 22 is adapted to receive a blood sample 12. The first chamber 22 includes a first chamber inlet 24 through which a whole blood sample is introduced and a first chamber outlet 26 through which a separated first portion of the blood sample exits the housing 20. The second chamber 28 includes a second chamber inlet which is directly adjacent the separation member 32 and a second chamber outlet 30. A separation member 32 is disposed between the first chamber 22 and the second chamber 28.

In one embodiment, the blood chamber 22 has a blood chamber length which is significantly longer than a height or width of the blood chamber 22 to improve the plasma separation efficiency. This may also increase a flow resistance of the blood, and thus require a higher pressure to drive the blood flow through the chamber. In one embodiment, a wider blood chamber can reduce flow resistance and the pressure needed to drive the blood flow. In some embodiments, the blood chamber geometry is balanced and/or configured for the targeted plasma yield and corresponding power source to operate the device.

Figure 4:
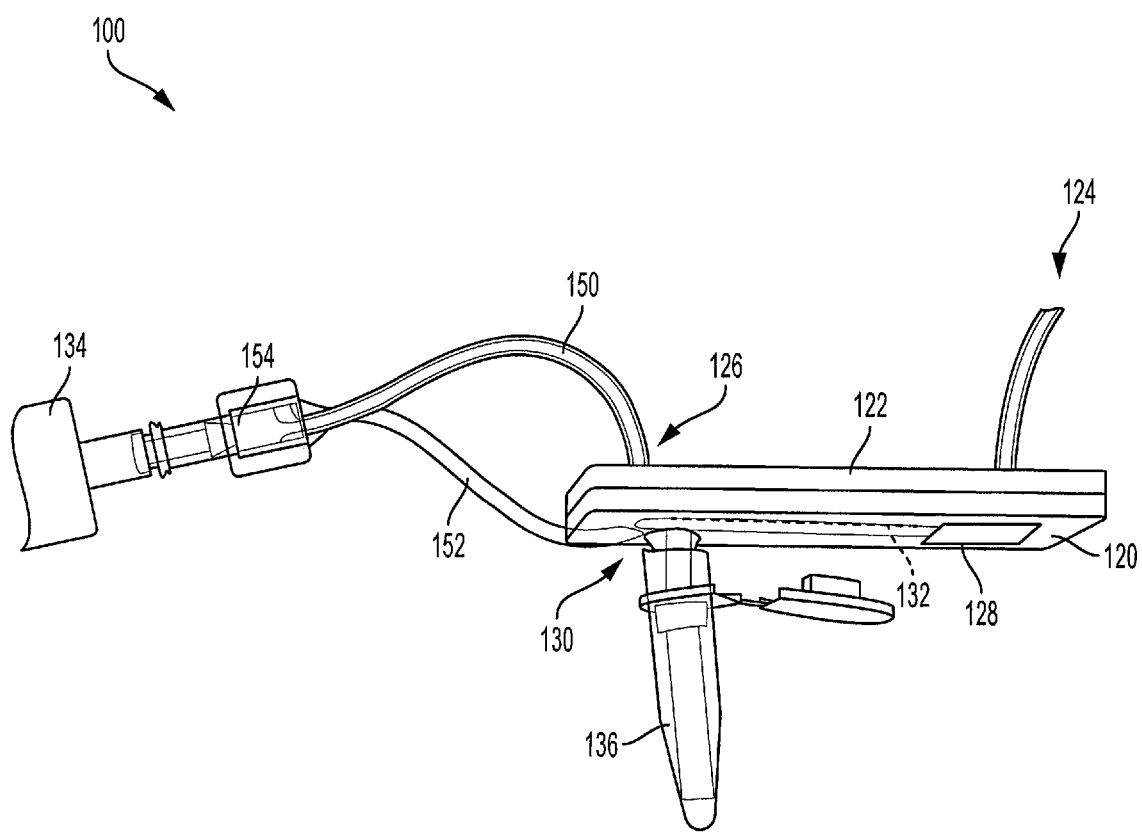
FIG. 4 is a perspective view of the blood separation device of FIG. 1 in accordance with an embodiment of the present invention.

The separation member 32 is adapted to restrain a first portion 14 or red blood cell portion of the blood sample 12 within the first chamber 22 and allow a second portion 16 or plasma portion to pass through the separation member 32 and into the second chamber 28, as shown in FIG. 2. Biological fluid, or blood, entering the first chamber 22 passes along the separation member 32 and the second portion 16 passes through the separation member 32 through the second chamber inlet and into the second chamber 28 while the first portion 14 is restrained with the first chamber 22. In one embodiment, the second chamber 28 may be a plasma collection container. In another embodiment, a plasma separation container 136, as shown in FIG. 4, may be provided in communication with the second chamber outlet 30.

The separation member 32 comprises a plurality of pores dimensioned to restrain the first portion 14 of the blood sample 12 and to allow the second portion 16 of the blood sample 12 to pass therethrough. In one configuration, the separation member 32 comprises a plurality of pores 53, as shown in FIG. 2, dimensioned to prevent red blood cells, white blood cells, platelets and fragments thereof (the first portion 14), from passing through the separation member 32, while allowing the plasma portion (the second portion 16) of the blood sample to pass through the separation member 32. Optionally, the separation member 32 may be a track-etched membrane. In one embodiment, the track-etched membrane comprises a polycarbonate membrane with a pore size of 0.4 µm and a pore density of $1.5 \times 10^8/cm^2$. In one embodiment, a separation member 32 includes a pore size from 0.2 to 1 µm. In one embodiment, a separation member 32 is formed of a material that can be PC, PET, PP, and/or combinations thereof. In one embodiment, the separation member 32 is substantially hydrophobic. In one embodiment, the pore density of a separation member 32 can be from $5 \times 10^8/cm^2$ to $1 \times 10^6/cm^2$. In one embodiment, the thickness of a separation member 32 can be from 8 to 100 µm. In one embodiment, the water flow rate of a separation member 32 can be in the range of 2.5 to 300 mL/min/cm$^2$ through the separation member 32.

In other embodiments, the separation member 32 may include hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 32 may comprise any filter that is able to trap the whole blood portion 14 in the first chamber 22 and allow the plasma portion 16 to pass through the separation member 32 and into the second chamber 28.

In one embodiment, the blood separation device 10 includes an actuator 34. The actuator 34 is in communication with a portion of the first chamber 22 and a portion of the second chamber 28. In one embodiment, actuation of the single actuator 34 imparts a pressure to a portion of the first chamber 22 to draw the biological fluid, such as the blood sample 12, into the first chamber 22. Actuation of the actuator 34 also imparts a pressure to a portion of the second chamber to draw at least a portion of the second portion 16 of the biological fluid into the second chamber 28. Accordingly, the actuation of the actuator 34 effectively draws the second portion 16 of the blood sample 12 through the separation member 32 as the blood sample 12 passes along the first chamber 22. The separation member 32 restrains the whole blood portion 14 in the first chamber 22 and allows the plasma portion 16 to pass through the separation member 32 and into the second chamber 28.

In one embodiment, the actuator 34 is a single actuator which provides a first pressure P1 to a portion of the first chamber 22 and a second pressure P2 to a portion of the second chamber 28, as shown in FIG. 1. In certain configurations, a vent 38 is provided in communication with a portion of the second chamber 28. The vent is transitionable between a closed position in which the vent seals the second chamber 28 and allows pressure P2 to be provided by the actuator 34 to the second chamber 28, and an open position in which the second chamber 28 is vented to atmosphere. The vent 38 may be provided in the closed position during separation of the second portion 16 of the biological fluid sample 12 from the first portion 14 of the biological fluid sample 12, and in the open position during removal of the second portion 16 of the biological fluid sample 12 from the second chamber 28, such as by disconnecting the plasma collection container 136, shown in FIG. 4.

Referring again to FIG. 1, the blood separation device 10 includes a blood chamber 22, a plasma chamber 28, and a separation member 32 that is operated by a pressure source, e.g., an actuator 34, to drive both blood flow and plasma flow. The actuator 34 may be a vacuum source. In some embodiments, the vacuum source can be from syringes, vacutainers, or other vacuum generators such as a Fluigent instrument. In other embodiments, a practical vacuum source can be achieved by using a syringe pulled manually or with a syringe pump to create the vacuum. The power source can also be a vacutainer, or other evacuated tube. In alternative embodiments, the plasma separation can be achieved by pushing blood from the blood inlet side, e.g., the first chamber inlet 24, to flow over the separation member 32. In this case the pressure source is a positive pressure which can be generated by syringes or compressed air or other gaseous medium.

In one embodiment, the blood flow and plasma separation using a blood separation device 10 of the present disclosure is powered by pressure at the inlet, e.g., the first chamber inlet 24, and the outlet, e.g., the first chamber outlet 26 and/or the second chamber outlet 30. In one embodiment, the pressure at the blood inlet, e.g., the first chamber inlet 24, may be set to zero and the pressure at the first chamber outlet 26 may be set at −5 psi. In one embodiment, the pressure at the plasma outlet, e.g., the second chamber outlet 30, may be set at −2 psi. In one embodiment, the pressure source is a vacuum source.

In one embodiment, the vent 38 is blocked during the plasma separation process and is optionally opened at the end of the plasma separation process to recover all of the plasma 16 from the plasma chamber 28. The pressure setting can be adjusted to specific flow (or shear) rate. In order to achieve short separation time, a higher flow rate and shear rate are desired. In one embodiment, a blood flow rate of 3 to 5 mL/min can be achieved using a blood separation device 10 of the present disclosure.

In one embodiment, the pressure source is the pressure to drive the blood flow and to create the trans-membrane pressure as the blood flows through the chamber. In one embodiment, the trans-membrane pressure should be large enough to drive the plasma flow through the separation member 32 but small enough to keep blood cells from being trapped at the pore entrance or dragged through the membrane pore. In one embodiment, the "net transmembrane pressure" should be less than 5 psi, preferably less than 2.5 psi.

In one embodiment, the pressure to drive the blood flow should be matched to the chamber geometry and targeted flow rate. The flow rate (more relevant to the fluid dynamics is the wall shear rate) should be uniform and large enough to prevent red blood cell deposit on to a membrane surface (cake layer formation). The shear rate should be below a threshold to prevent shear induced hemolysis. This shear induced hemolysis is also dependent on residence time under the shear. The combination effect from shear and time should be controlled.

A blood separation device 10 of the present disclosure provides a balanced blood chamber with a large chamber length, a small chamber height, and a large chamber width that has a great separation efficiency. The pressure settings allow for a high flow rate and shear rate within a design target of separation time and input blood volume. Pressure settings also allow proper transmembrane pressure during the separation process. The shear rate prevents blood cake formation as blood flows through the chamber over the membrane surface.

Referring again to FIG. 1, use of a blood separation device 10 of the present disclosure will now be described. In one embodiment, as described above, the blood separation device 10 includes a blood chamber 22 and a plasma chamber 28 which are separated by a separation member or membrane 32, e.g., a track etched membrane. In one embodiment, the membrane 32 is part of the blood chamber 22 and at the same time part of the plasma chamber 28. The blood chamber 22 has a blood inlet, e.g., a first chamber inlet 24, and an outlet, e.g., a first chamber outlet 26. The plasma chamber 28 has one or multiple outlets, e.g., a second chamber outlet 30. Blood flows in through the inlet 24 of the blood chamber 22 and tangentially over the membrane 32 surface, and exits from the outlet 26 of the blood chamber 22. Plasma 16 flows through the membrane 32 and enters the plasma chamber 28 which can be collected or stored in a secondary plasma container, e.g., a plasma collection container 36, for further diagnostic tests. For example, in one embodiment, after separation, the blood separation device 10 is able to transfer the plasma portion of the blood sample to a point-of-care testing device.

Figure 3:
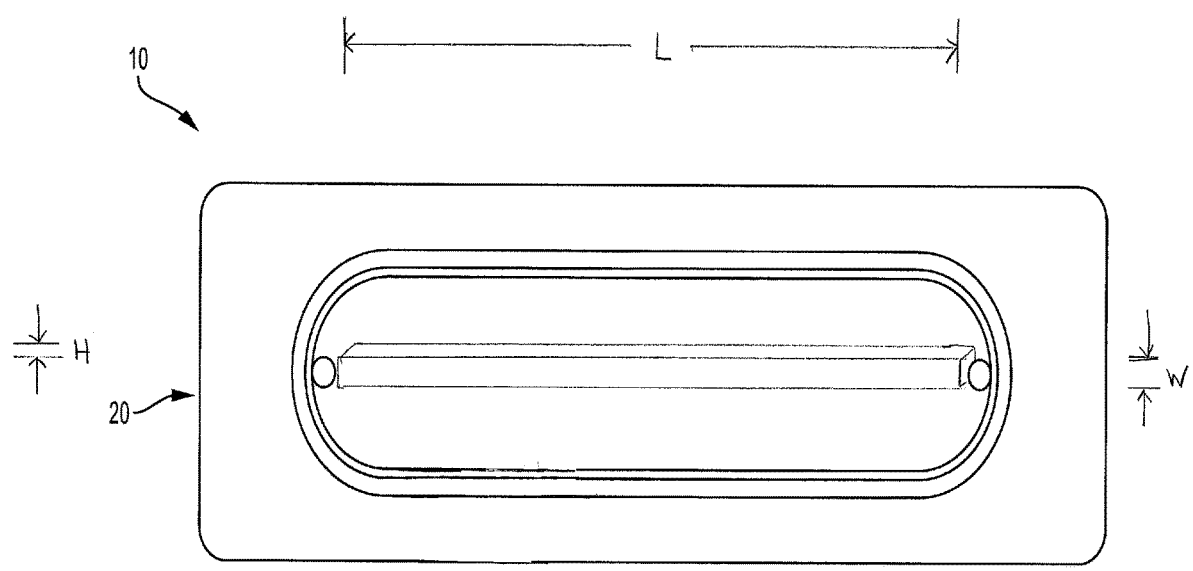
FIG. 3 is a top view of the housing of the blood separation device of FIG. 1 in accordance with an embodiment of the present invention.

In one embodiment, the blood chamber 22 can be designed to allow tangential flow of the blood over the membrane 32 surface which can have different shapes such as but not limited to rectangular, spiral, or serpentine etc. The size of the chamber can be varied to meet the application needs for the plasma volume. The inlet 24 and outlet 26 of the blood chamber 22 may be at a non-filtration area to maximize the tangential flow. In one embodiment, the plasma chamber 28 may match the blood chamber 22 to allow efficient utilization of the membrane 32. In one embodiment, referring to FIG. 3, a design example may include a rectangular chamber.

In one exemplary embodiment, the blood chamber 22 was a width W of 10 mm, and a length L of 50 mm with the inlet 24 and the outlet 26 at each end of the blood chamber 22. In one embodiment, the blood chamber 22 has a height H that is 0.08 μm. In one embodiment, the plasma chamber has a length L of 10 mm, a width W of 4 mm, and a height H of 0.2 μm. In one embodiment, ridges are created inside the plasma chamber 28 to support the membrane 32. The membrane 32 can be optionally secured onto the ridges to prevent sagging. Alternatively the ridges can be built in the blood chamber 22 or on both chambers. In one embodiment, the track-etched membrane is a polycarbonate membrane with a pore size of 0.4 μm and pore density of $1.5 \times 10^8/cm^2$.

FIG. 4 illustrates another exemplary embodiment of a blood separation device of the present disclosure. Referring to FIGS. 4 and 2, a blood separation device 100 of the present disclosure is adapted to receive a blood sample 12 having a whole blood portion 14 and a plasma portion 16. The present disclosure provides a blood separation device and a separation process that allows high quality plasma to be generated in less than 1 minute and a blood separation device that allows a single pressure source such as a vacutainer tube to power the whole plasma separation process. The device design is simple, low cost, and disposable. The plasma separation process is fast, easy to operate, and produces high quality plasma samples from whole blood. It is scalable from sample size of micron liters to milliliters. The separation process does not require any hardware or electric power. It is operated by pressures which can be generated by using a syringe draw and/or a vacutainer tube. The quality of the separated plasma is comparable to that of tube plasma generated by centrifugation and suitable for various diagnostic needs.

In one embodiment, after collecting a blood sample, the blood separation device 100 is able to separate a plasma portion of the blood sample from the whole blood portion as described in more detail below. In one embodiment, after separation, the blood separation device 100 is able to transfer the plasma portion of the blood sample to a point-of-care testing device.

Referring to FIG. 4, a blood separation device 100 generally includes a housing 120, a first chamber or blood chamber 122, a first chamber inlet 124, a first chamber outlet 126, a second chamber or plasma chamber 128, a second chamber outlet 130, a separation member or membrane 132, an actuator 134, a plasma collection container 136, a first line or blood line 150, a second line or plasma line 152, and a merged line 154. In one embodiment, the first line 150 and the second line 152 are merged into line 154.

In one embodiment, the housing 120 defines a first chamber 122 and a second chamber 128. The first chamber 122 is adapted to receive a blood sample 12. The first chamber 122 includes a first chamber inlet 124 and a first chamber outlet 126. The second chamber 128 includes a second chamber outlet 130. In one embodiment, the blood separation device 100 includes a separation member 132 that is disposed between the first chamber 122 and the second chamber 128.

The separation member 132 is adapted to trap the whole blood portion 14 in the first chamber 122 and allow the plasma portion 16 to pass through the separation member 132 and into the second chamber 128, as shown in FIG. 2.

In one embodiment, the separation member 132 comprises a track-etched membrane. In one embodiment, the track-etched membrane comprises a polycarbonate membrane with a pore size of 0.4 μm and a pore density of $1.5\times10^8/cm^2$. In one embodiment, a separation member 132 includes a pore size from 0.2 to 1 μm. In one embodiment, a separation member 132 is formed of a material that can be PC, PET, PP, or other materials. In one embodiment, a separation member 132 is hydrophobic. In one embodiment, the pore density of a separation member 132 can be from $5\times10^8/cm^2$ to $1\times10^6/cm^2$. In one embodiment, the thickness of a separation member 132 can be from 8 to 100 μm. In one embodiment, the water flow rate of a separation member 132 can be in the range of 2.5 to 300 mL/min/cm$^2$ through the separation member 132.

In other embodiments, the separation member 132 may be either hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 132 may comprise any filter that is able to trap the whole blood portion 14 in the first chamber 122 and allow the plasma portion 16 to pass through the separation member 132 and into the second chamber 128.

In one embodiment, a first line 150 is in communication with the actuator 134 and the first chamber outlet 126. In one embodiment, a second line 152 is in communication with the actuator 134 and the second chamber outlet 130.

In one embodiment, the blood separation device 100 includes a plasma collection container 136 that is in communication with the second chamber outlet 130. The plasma collection container 136 is able to collect and store the separated plasma 16.

In one embodiment, the blood separation device 100 includes a porous material within the second line 152.

In one embodiment, the blood separation device 100 includes an actuator 134. The actuator 134 is in communication with a portion of the first chamber 122 via the first line 150 and a portion of the second chamber 128 via the second line 152. In one embodiment, actuation of the actuator 134 draws a blood sample 12 into the first chamber 122 and the separation member 132 is adapted to allow the plasma portion 16 of the blood sample 12 to pass through the separation member 132 to the second chamber 128. In one embodiment, the separation member 132 is adapted to trap the whole blood portion 14 in the first chamber 122 and allow the plasma portion 16 to pass through the separation member 132 and into the second chamber 128.

In one embodiment, the blood separation device 100 includes a blood chamber 122, a plasma chamber 128, and a separation member 132 that is operated by a pressure source, e.g., an actuator 134, to drive the blood flow and plasma flow. In one embodiment, the actuator 134 is a vacuum source.

In one embodiment, a single actuator provides a first pressure to a portion of the first chamber 122 via the first line 150 and a second pressure to a portion of the second chamber 128 via the second line 152.

The blood separation device 100 with lines 150, 152 provides a system that requires only one pressure source to drive both blood and plasma sides of the device. The blood separation device 100 merges two lines 150, 152 into one merged line 154. In one embodiment, a porous material is added to the plasma vacuum line 152 to create air flow resistance. When a vacuum source is connected to the merged vacuum line 154, a majority of the power source is directed to the blood chamber 122 through line 150 and powers the blood flow. A small portion of the vacuum is directed to the plasma chamber 128 through line 152 to drive the plasma flow and trans-membrane pressure. The resister may be a porous polymeric disc with 1 micron meter pore size, such as those commercially available from Porax. It is noted, however, that the porous material can be in many forms such as fiber, sintered polymeric materials, porous metals, or any other air permeable materials. Alternatively, it can also be a small tube or channel built on a device that resists air flow. The merger for the two vacuum lines and porous material can also be built or incorporated on the device directly.

An alternative design of the blood separation device 100 may incorporate a blood reservoir similar to the plasma reservoir for collecting blood waste, instead of using a vacutainer tube as the reservoir for the waste blood. This may be beneficial when a centralized vacuum source is used.

Advantageously, the blood separation device 100 of the present disclosure allows a single pressure source to power the whole plasma separation process.

In one embodiment, the device design parameters (balanced blood chamber height, width, and length) match the process parameter settings (Pressures P1 and P2 for driving blood flow and for providing trans-membrane pressure, respectively). The matched system provides targeted flow rate and shear rate so that the cake formation is prevented on a membrane surface. The trans-membrane pressure drives plasma flow through the membrane. If the design and process parameters are not matched, the plasma yield will be low and/or hemolysis will occur. This matching is dominated by the design parameters if a certain flow rate and the uniformity of trans-membrane pressure along the length of the membrane are to be achieved. The trans-membrane pressure uniformity is affected by the pressure drop along the chamber length in the blood chamber.

In one embodiment, the flow resister design and its incorporation in the device allow one single pressure source to drive blood flow and form the trans-membrane pressure. The resister allows a small portion of the common vacuum source to be directed to the plasma side and provide sufficient pressure to drive the plasma flow. The flow resister is built in such a manner that it allows the restriction of airflow in the plasma side but does not get into the plasma path. This simplifies the power source requirement and plasma separation process. For example, the plasma separation can be achieved by connecting the device to a blood source and pushing a vacutainer to the device. Plasma is separated in less than one minute. This result is considered exceptional when compared with prior designs which provide slow methodology and a low yield of plasma, such as a production value of 50 µL or less plasma in 10 minutes.

A blood separation device of the present disclosure provides a significantly improved performance. The device and method of the present disclosure produces about 400 µL plasma in less than 1 minute using one third of the membrane size of prior designs. In one embodiment, the blood separation device of the present disclosure uses a blood chamber size of 10 mm×50 mm×0.08 mm and a plasma chamber size of 10 mm×40 mm×0.2 mm with an effective separation membrane area of 10 mm×40 mm. The blood flow rate is 3 mL/min and the pressure settings are 5 psi vacuum for blood side and 2 psi vacuum for the plasma side. The input blood is at 38% hematocrit. The process generated about 400 µL high quality plasma in one minute with very low hemolysis as indicated by low hemoglobin level in the plasma samples, as shown in FIG. 5. FIG. 5 illustrates plasma separation performance using a blood separation device of the present disclosure with normal heparinized whole blood at 38% hematocrit.

Plasma samples separated by using the method and blood separation device of the present disclosure are also analyzed using Sysmex to determine the residue cells. The purity of the plasma is comparable to the control sample obtained by conventional centrifugation process, as shown in FIG. 6. Blood samples from different donors were tested and all performed consistently on a blood separation device of the present disclosure. FIG. 6 illustrates plasma purity determined by Sysmex for samples separated using a blood separation device of the present disclosure with normal heparinized whole blood at 46% hematocrit. The method and blood separation device of the present disclosure also performs very well with whole blood at higher hematocrit (55%). The yield is about 250 µL with the input volume of 3 mL as shown in FIG. 6.

Figures 7, 8:
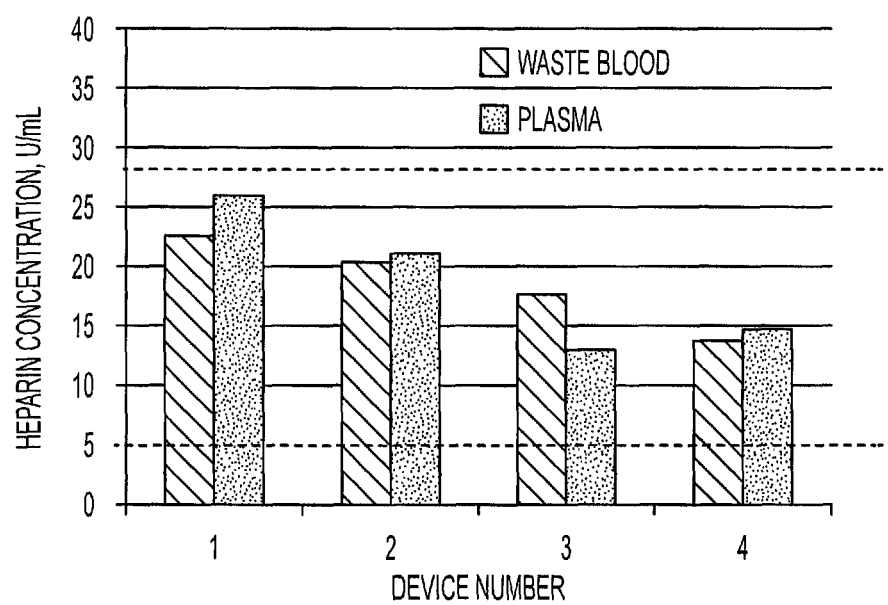
FIG. 7 is a table listing the input blood volume and output plasma volume of performance testing of the device of FIG. 1 in accordance with an embodiment of the present invention.
FIG. 8 is a graph illustrating the resulting output plasma and waste blood portions as a function of Heparin concentration as a result of performance testing of the device of FIG. 1 in accordance with an embodiment of the present invention.

FIG. 7 illustrates plasma separation performance using a blood separation device of the present disclosure with heparinized whole blood at 55% hematocrit. The plasma samples also have very low hemolysis for high hematocrit input blood sample.

Plasma separation was also conducted successfully using the method and blood separation device of the present disclosure with normal fresh blood with no anticoagulant added prior to plasma separation. This allows the device of the present disclosure to work with blood samples directly from line draw without the need to add anticoagulant to the blood sample. When the device is loaded with heparin in the chambers at target dosage, it can stabilize the blood and plasma during the separation process. The heparin concentration can be designed to match the tube blood specification of 5 to 28 IU/mL. The plasma samples produced are stable and suitable for further diagnostic purpose. The data from FIG. 8 is obtained using a heparin activity test.

FIG. 8 illustrates plasma separation conducted successfully using the method and blood separation device of the present disclosure with normal fresh blood (no anticoagulant added prior to plasma separation) at 42.6% hematocrit. The anticoagulant (heparin) is applied on device chambers and mixed into blood and plasma during plasma separation process. It is also noted herein that a biological fluid separation device 10 of the present disclosure could be used for other sample management purposes such as cell isolation, purification, and sample concentration.

It is noted herein that plasma generated using this invention contains diagnostically relevant analytes. Examples of analytes that can be tested directly from plasma separated using this technology include, but are not limited to those in general chemistry panels (e.g. potassium, sodium, calcium, magnesium, chloride, phosphate), triglycerides, cholesterol, high density lipoprotein (HDL)-cholesterol, low density lipoprotein (LDL)-cholesterol, C-reactive protein (CRP), aspartate transaminase/glutamic-oxaloacetic transaminase (AST/GOT), lipase, albumin, bilirubin, glucose, creatinine, IgG, ferritine, insulin, rheumatoid factors and prostate-specific antigen (PSA); hormones such as thyroid-stimulating hormone (TSH), free T3 Total T3, Free T4, Total T4, follicle-stimulating hormone (FSH) and beta human chorionic gondatropin (hCG); vitamins such as Vitamin D and Vitamin B12; and cardiac markers such as Troponin (cTnI, cTnT), b-type-natriuretic-peptide (BNP), NTproBNP, D-dimer, creatine kinase (CK), CK-MB, myoglobin. Additional analytes that can be tested from plasma separated using this technology include, but are not limited to nucleic acids (e.g. circulating cell-free DNA, microRNAs), exosomes, DNA viruses (e.g. Hepatitis-B) and RNA viruses (e.g. HIV).

Referring to FIGS. 9-13, another aspect of the present disclosure is a suite of fast-running, in-silica, analytical models that couples the physics of cross-flow filtration, fluid dynamics transport, and hemolysis from filtration and shear forces. Such models calculate: (A) a representative viscosity of human blood under high shear rate conditions as a function of hematocrit; (B) a representative pressure drop, flow rate, wall shear stress, wall shear rate, and representative fluid residence time in rectangular channel above the filtration surface; (C) the volume of plasma generated by cross flow filtration through a filtration membrane with a representative pore radius and the plasma volumetric flow rate through the filtration surface; and (D) a risk assessment of hemolysis caused by shear and filtration forces.

In one embodiment, the models of the present disclosure may be coded into the scientific computer language MATLAB and are from a trained user who specifies the model inputs and executes the analysis. Calculations are performed in less than one minute and the user has rapid feedback on the feasibility of a design's geometry and/or operating conditions based on the potential volume of generated plasma, required fluid dynamics (flow, pressure, and shear), and hemolysis risk.

The models of the present disclosure are advantageous in that they are capable of providing the same breadth of information in a much shorter time. For example, existing models that provide the same breadth of information take weeks or even months to complete a single calculation or assessment of a single geometry. Moreover, the prior art models require many more additional parameters that each require their own detailed investigation to determine appropriate values. Conversely, existing fast-running models target an individual physics area and do not couple or consider other physics at work (e.g., the filtration performance on the local fluid dynamics environment or hemolysis dependency on both the local fluid dynamics and filtration conditions).

Another improvement of the models of the present disclosure is implementing all calculations in MATLAB using function-based and calculation script(s) arrangements. The coding style leverages plug-and-play capability from object-oriented programming techniques for future uses. Additionally, the MATLAB code was structured to enable rapid explorations of large design spaces through probabilistic or optimization techniques.

Previous prior art models have one or more of the following limitations: (1) too long of a run time, (2) do not provide enough information, (3) are too simplistic, and/or (4) are not implemented in a format that can be leveraged for automated explorations of possible design spaces.

The models of the present disclosure provide a balance of run time and model accuracy/complexity that has been achieved through selecting fast running analytical models and target key enhancements that are applicable to plasma filtration from undiluted whole blood. Enabling automated explorations was enabled through implementing the models in the MATLAB scientific computing language using good practices of memory management and code development for robustness and plug-and-play capabilities.

The nature of the developed model is to make some large simplifying assumptions that would enable this relationship to be included in analytical fluid dynamic calculations that require a constant viscosity. The technique allows viscosity to vary with hematocrit but keeps viscosity constant under the different fluidic forces at work during the flow of blood in rectangular microchannels.

The assumptions that enable the mathematical derivation of the analytical models include: constant fluid properties under fluidic forces of shear and pressure, no gravitational forces, full-developed flow, steady (constant/unchanging) flow conditions with respect to time, and that blood flow occurs in channels with a rectangular cross-section.

The hemolysis models are designed to capture the dependence of red blood cell damage as a function of mechanical load and exposure time. The two mechanical loading mechanisms included in the suite of models are shear stress caused by general fluid flow and filtration forces caused by cells entrapped within the pores of the filtration membrane. Fluid shear stress is primarily considered at the nonmoving walls where the shear forces are at their maximum value.

A threshold value of shear stress and exposure time was used as one hemolysis criteria for human red blood cells. A second hemolysis criterion was a model for the mechanical loading of red blood cell membrane caused by cellular entrapment in the filtration pores. Thus, the two fluidic values that are assessed whether they are below the calculated hemolysis thresholds are the wall shear stress and the pressure drop along the microchannel length.

The suite of models was also supported with empirical data that the mechanical forces from filtration and filtration membrane pore clogging have a higher hemolysis risk than shear induced hemolysis from bulk fluid shear forces.

The models of the present disclosure include a suite of analytical models for a single pass cross-flow filtration. The models of the present disclosure provide an enhanced analytical modeling introduction having an intended use for the explorations of broad ranges of operational and design parameters, prioritizes speed over accuracy, and attempts to enhance accuracy with targeted model improvements that still maintain fast calculation times.

Figure 9:
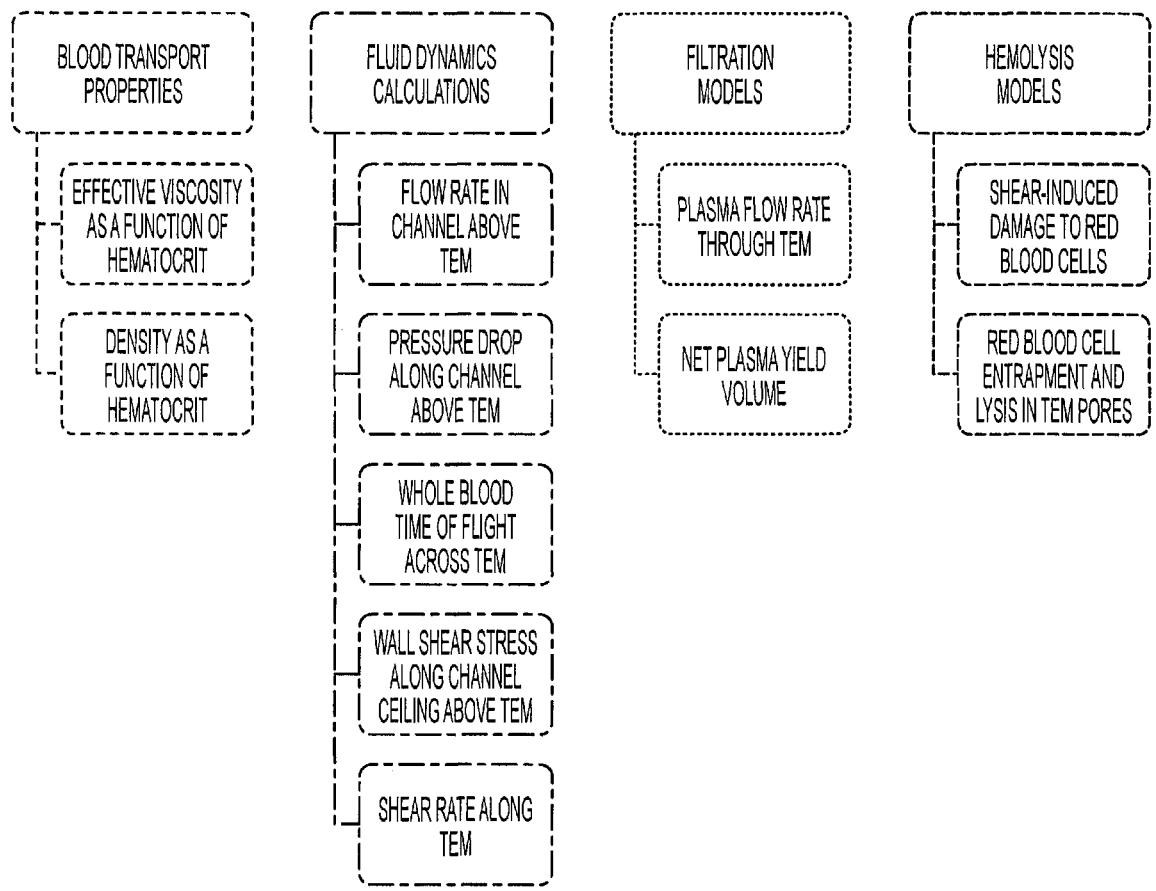
FIG. 9 is a flow chart illustrating exemplary modeling in accordance with an embodiment of the present invention.

Referring to FIG. 9, a first flow chart of an exemplary considerations of the present disclosure is illustrated.

Figure 10:
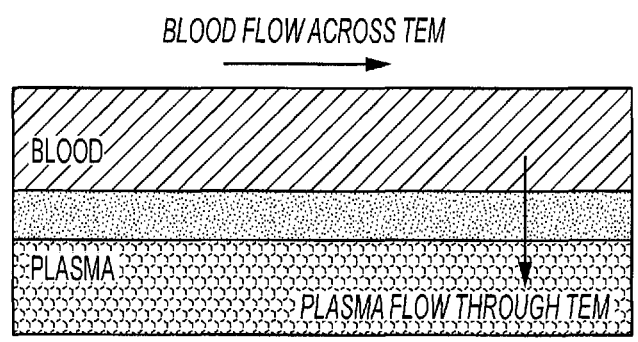
FIG. 10 is a schematic representation illustrating a track-etch membrane for a blood separation device in accordance with an embodiment of the present invention.

Referring to FIG. 10, a cross-flow filtration concept of the present disclosure includes a track-etch membrane (TEM), the pressure drop along the channel above the TEM contributes to the transmembrane pressure that drives plasma through the TEM, and the flow across the TEM helps prevent pore clogging and membrane fouling.

In one embodiment, inputs to the suite of analytical models and calculations include (1) whole blood hematocrit prior to filtration, (2) dimensions of channel above TEM including height, width, and length, (3) duration (time) of filtration, and (4) flow conditions including blood volumetric flow rate across TEM, the pressure drop along channel above TEM, and the volume of blood to be transported over the TEM during the time of filtration.

In one embodiment, outputs to the suite of analytical models and calculations include (1) plasma flow rate through the TEM, (2) net plasma yield volume after the duration of filtration, and (3) hemolysis potential through fluid shear stress and red blood cell entrapment within TEM pores including ensuring wall shear stress is below published critical values (1500 dyne/cm$^2$) and ensuring shear rate along TEM and maximum transmembrane pressure keeps red blood cell membrane tension below critical value.

Figure 11:
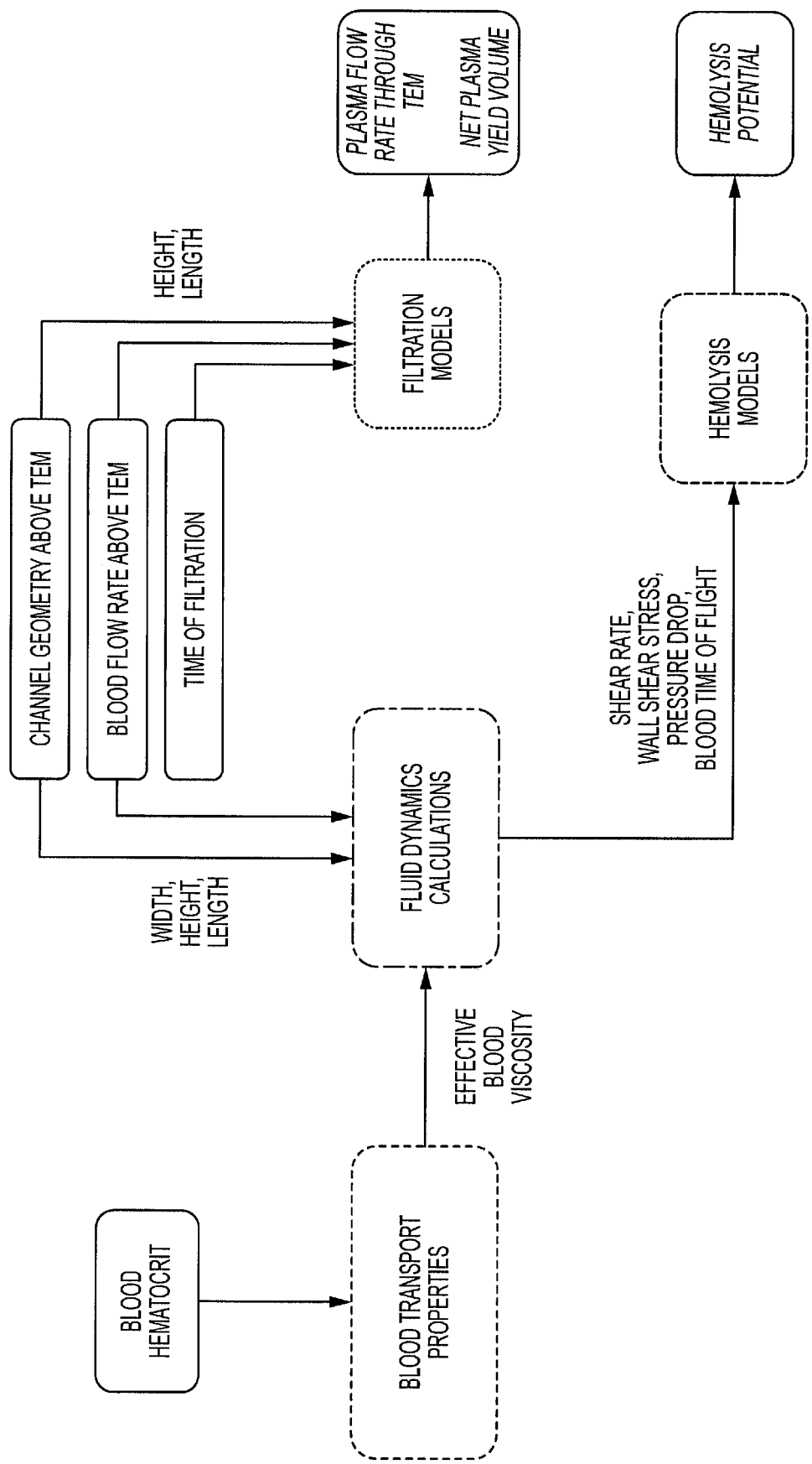
FIG. 11 is a flow chart illustrating exemplary modeling in accordance with an embodiment of the present invention.
Figure 12:
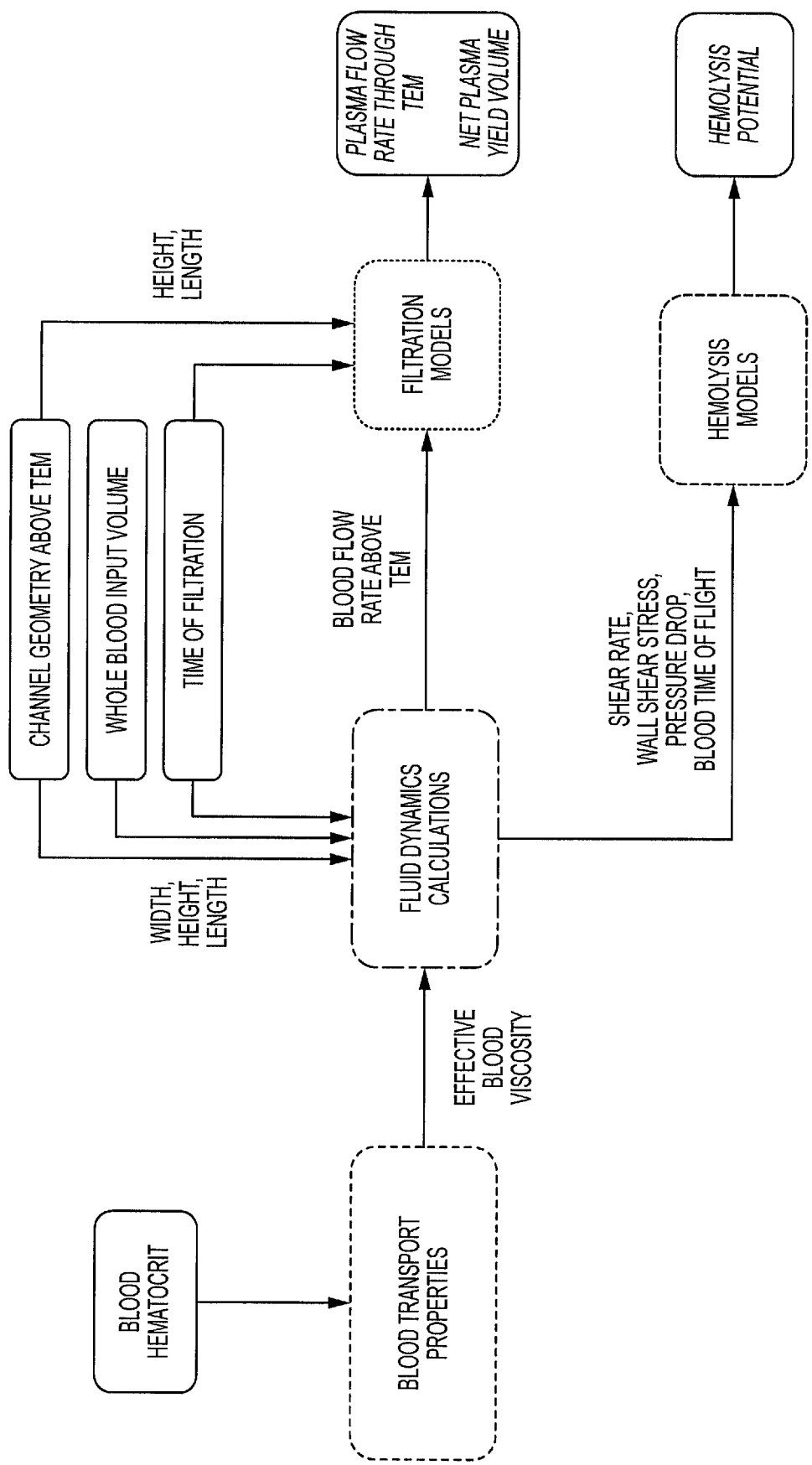
FIG. 12 is a flow chart illustrating exemplary modeling in accordance with an embodiment of the present invention.
Figure 13:
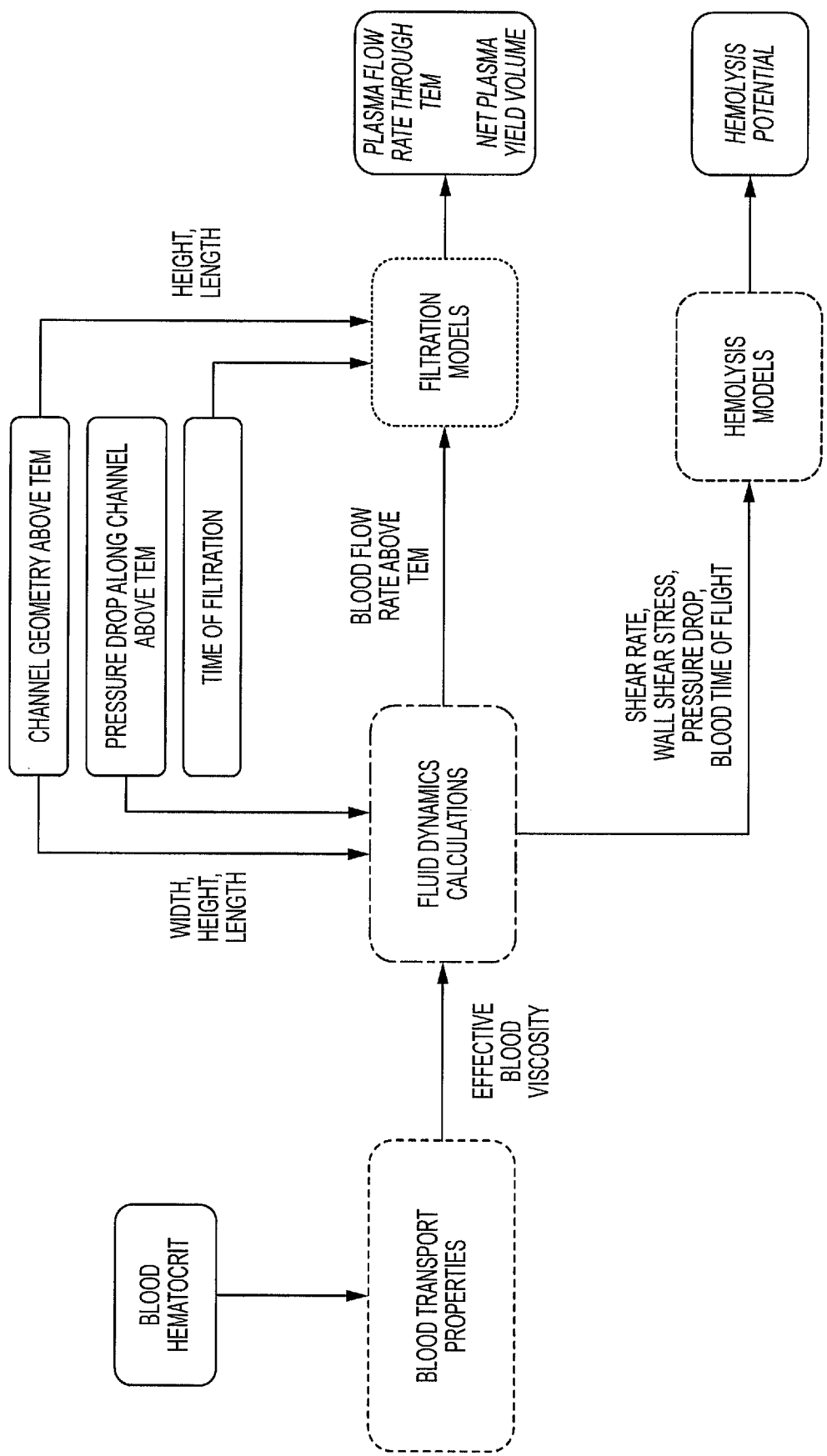
FIG. 13 is a flow chart illustrating exemplary modeling in accordance with an embodiment of the present invention.

Referring to FIGS. 11-13, additional flow charts of exemplary embodiments of the present disclosure are illustrated.

The models of the present disclosure include the following calculation assumptions and limitations. The blood transport has a viscosity that is dependent on hematocrit only and the density is calculated using a linear rule of mixtures. The fluid dynamics calculations include the following: (1) a channel that has a rectangular cross section, (2) steady-state conditions that are constant over time, (3) a constant hematocrit over all channel dimensions, (4) a flow rate across TEM that is not decreased over a TEM length, and (5) a TEM width and length that is equal to the channel width and length. The filtration model includes (1) a TEM that is already wetted, (2) steady-state conditions that are constant over time, (3) a channel width only included in the flow rate across TEM, (4) uses flow rate across TEM and not transmembrane pressure, and (5) no cake layer formation is included in plasma flow rate or yield volume calculations. The hemolysis models include that the contact time between the cells and TEM is linearly related to the inverse of the shear rate along the TEM and a pressure drop along the channel above TEM is equal to the maximum transmembrane pressure.

The models of the present disclosure include the following recommended uses: (1) reduce the selected operating parameters' risk of hemolysis due to red blood shear stress and red blood cell entrapment, (2) balance or tune system physics: flow rates in channel above membrane with reduced risk of hemolysis but generate sufficient volume of filtered plasma, pressure drop and flow rate in different sized channels, and maximize plasma volume while ensuring minimal hemolysis, and (3) determine the amount of blood to flow over membrane to generate sufficient volume of filtered plasma.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid separation device adapted to receive a biological fluid sample having a first portion and a second portion, the biological fluid separation device comprising:
   a housing, comprising:
   a first chamber having a first chamber inlet for receiving the biological fluid sample therein and a first chamber outlet wherein the first chamber outlet is placed a lateral distance from the first chamber inlet in the first chamber, a second chamber having a second chamber inlet and a second chamber outlet, and a separation member separating a portion of the first chamber and the second chamber such that the first chamber includes a filtration area underneath the separation member and a non-filtration area that is not underneath the separation member, wherein the first chamber inlet and the first chamber outlet are each placed in a different portion of the non-filtration area, wherein the separation member defines a tangential flow path along the lateral distance from the first chamber inlet to the first chamber outlet and is adapted to restrain the first portion of the biological fluid sample within the first chamber and to allow at least a portion of the second portion of the biological fluid sample to pass into the second chamber; and an actuator in communication with a portion of the housing, wherein the actuator is a vacuum source that provides a first pressure at the first chamber outlet and a second pressure at the second chamber outlet, wherein the first pressure is different from the second pressure and wherein, in response to the actuator, the biological fluid sample is drawn into the first chamber.

2. The biological fluid separation device of claim 1, wherein the biological fluid sample is whole blood, the first portion is a red blood cell portion and the second portion is a plasma portion.

3. The biological fluid separation device of claim 1, wherein actuation of the actuator draws the second portion of the biological fluid sample through the separation member.

4. The biological fluid separation device of claim 1, wherein the vacuum source is an evacuated tube.

5. The biological fluid separation device of claim 1, wherein the second chamber is a plasma collection container.

6. The biological fluid separation device of claim 1, further comprising a plasma collection container in communication with the second chamber.

7. The biological fluid separation device of claim 1, wherein the actuator is a single actuator in communication with the first chamber and the second chamber and which imparts a pressure to a portion of the first chamber to draw the biological fluid sample into the first chamber, and imparts another pressure to a portion of the second chamber to draw a portion of the second portion of the biological fluid sample into the second chamber.

8. The biological fluid separation device of claim 1, wherein the separation member comprises a track-etched membrane.

9. The biological fluid separation device of claim 8, wherein the track-etched membrane is a polycarbonate membrane.

10. The biological fluid separation device of claim 1, further comprising a vent in communication with a portion of the second chamber, the vent transitionable between a closed position in which the vent seals the second chamber, and an open position in which the second chamber is vented to atmosphere.

11. The biological fluid separation device of claim 10, wherein the vent is provided in the closed position during separation of the second portion of the biological fluid sample from the first portion of the biological fluid sample, and in the open position during removal of the second portion of the biological fluid sample from the second chamber.

* * * * *